US00PP37144P2

(12) United States Plant Patent
Holtmaat

(10) Patent No.: US PP37,144 P2
(45) Date of Patent: Dec. 9, 2025

(54) ***SEDUM* PLANT NAMED 'PPC093'**

(50) Latin Name: ***Sedum* hybrid**
Varietal Denomination: PPC093

(71) Applicant: Henricus Maria Joseph Holtmaat, Zuidwolde (NL)

(72) Inventor: Henricus Maria Joseph Holtmaat, Zuidwolde (NL)

(73) Assignee: AB KWEKERSRECHTEN B.V., Zuidwolde (NL)

( * ) Notice: Subject to any disclaimer, the term of this patent is extended or adjusted under 35 U.S.C. 154(b) by 0 days.

(21) Appl. No.: 19/177,619

(22) Filed: Apr. 13, 2025

(51) Int. Cl.
*A01H 5/02* (2018.01)
*A01H 6/32* (2018.01)

(52) U.S. Cl.
USPC ..... Plt./479

(58) Field of Classification Search
USPC ..... Plt./263.1, 479
See application file for complete search history.

(56) References Cited

U.S. PATENT DOCUMENTS

PP26,078 P3 * 11/2015 Egger ..... A01H 5/02
Plt./479

* cited by examiner

*Primary Examiner* — Karen M Redden
(74) *Attorney, Agent, or Firm* — Penny J. Aguirre

(57) ABSTRACT

A new cultivar of *Sedum* plant named 'PPC093' that is characterized by its short plant height, its mature foliage that is purple in color, and its flowers that are yellow and grey-purple in color.

3 Drawing Sheets

CROSS REFERENCE TO A RELATED APPLICATION

This application is co-pending with a U.S. Plant Patent Applications filed for plants derived from the same breeding program that is entitled Sedum Plant Named 'PPF095' (U. S. Plant Patent application Ser. No. 19/177,624).

Botanical classification: *Sedum* hybrid.

Variety denomination: 'PPC093'.

BACKGROUND OF THE INVENTION

The present invention relates to a new and distinct cultivar of *Sedum* plant, botanically of hybrid origin and known as *Sedum* 'PPC093' referred to hereinafter by its cultivar name, 'PPC093'. The new cultivar of *Sedum* is a hardy herbaceous perennial grown for use as a landscape and container plant.

The new cultivar arose from an ongoing breeding program conducted by the Inventor in Zuidwolde, The Netherlands. The Inventor collected and sowed seeds from open pollination of numerous unnamed and unpatented proprietary *Sedum* plants from the Inventor's breeding program. The seeds were pooled prior to sowing, therefore the parentage of 'PPC093' is unknown. 'PPC093' was selected as a single unique plant from the resulting seedlings in August 2020.

Asexual propagation of the new cultivar was first accomplished under the direction of the Inventor by tissue culture using meristematic tissue in March 2022 in Heerhugowaard, The Netherlands. Asexual propagation by tissue culture and stem cuttings has determined the characteristics to be stable and reproduced true to type in successive generations.

SUMMARY OF THE INVENTION

The following traits have been repeatedly observed and are determined to be the characteristics of the new cultivar. These attributes in combination distinguish 'PPC093' as a unique cultivar of *Sedum*.

1. 'PPC093' exhibits a short plant height.
2. 'PPC093' exhibits mature foliage that is purple in color.
3. 'PPC093' exhibits flowers that are yellow and grey-purple in color.

'PPC093' can be compared to *Sedum* cultivars 'Olek 6' (not patented), 'Mojave Jewels Sapphire' (not patented) and 'PPF095'. All are similar to 'PPC093' in having dark colored foliage. 'Olek 6' differs in having a shorter plant height and flowers that are pink in color. 'Mojave Jewels Sapphire' differs from 'PPC093' in having a taller plant height and flowers that are red in color. 'PPF095' differs from 'PPC093' in having foliage and stems that are darker in color and flowers that are red in color.

BRIEF DESCRIPTION OF THE DRAWINGS

The accompanying color photographs illustrate the overall appearance and distinct characteristics of the new *Sedum*. The photographs were taken of a plant 2 years in age as field grown in Zuidwolde, The Netherlands and placed in a 27-cm container for the photographs. The photograph in FIG. 1 provides a side view of 'PPC093' in bloom.

The photograph in FIG. 2 provides a view of the inflorescences of 'PPC093'.

Figure 1:
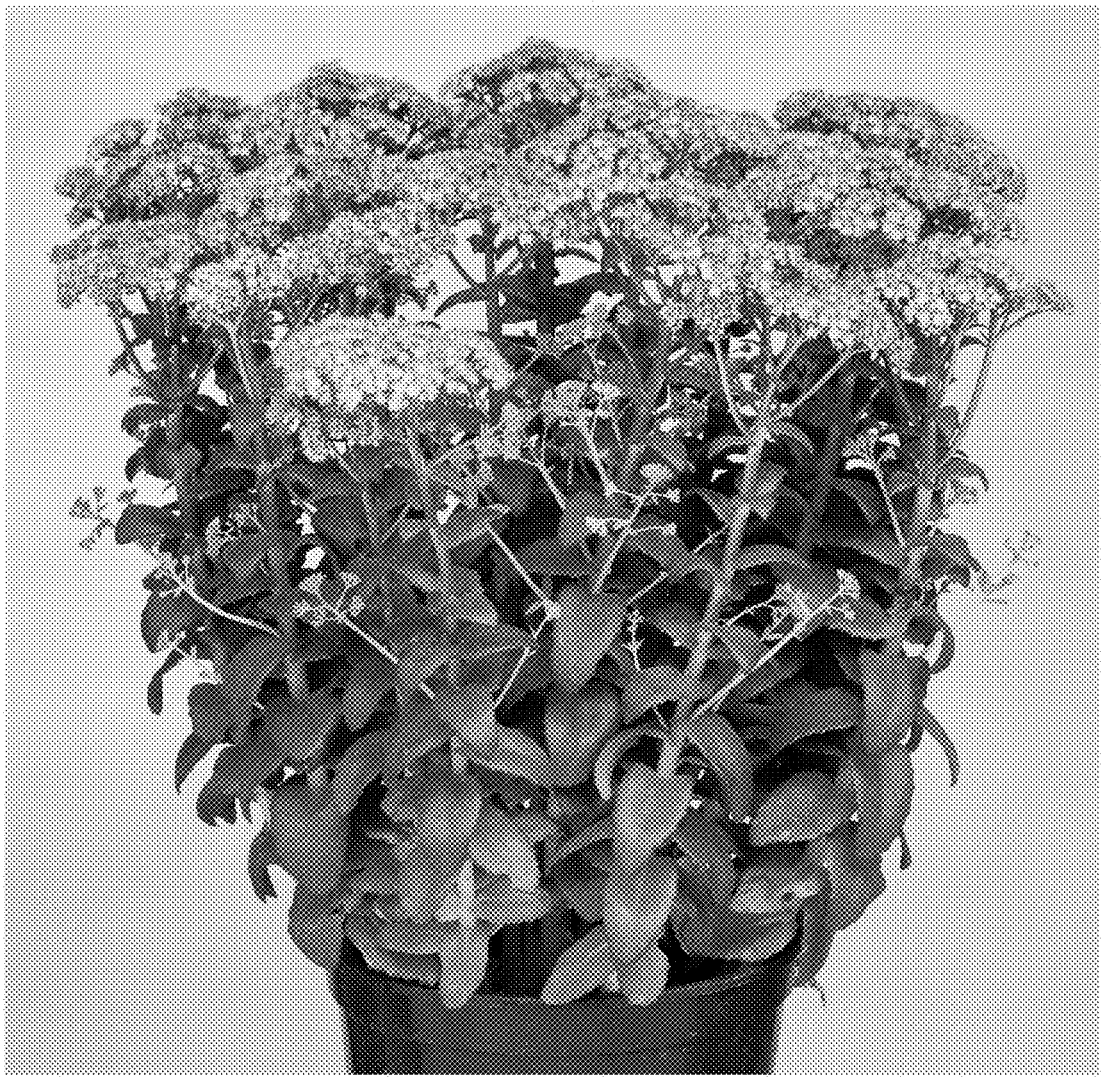
Figure 2:
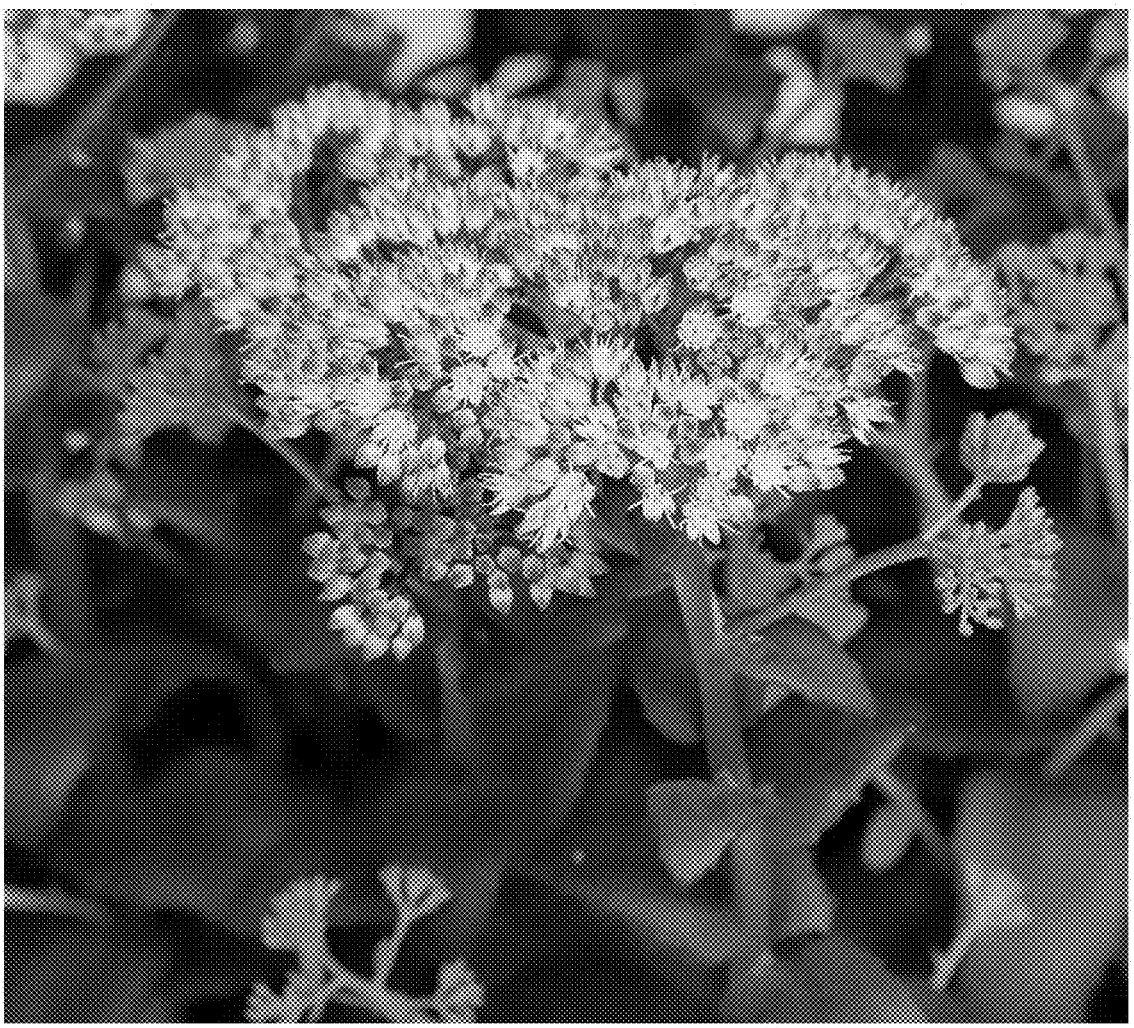
Figure 3:
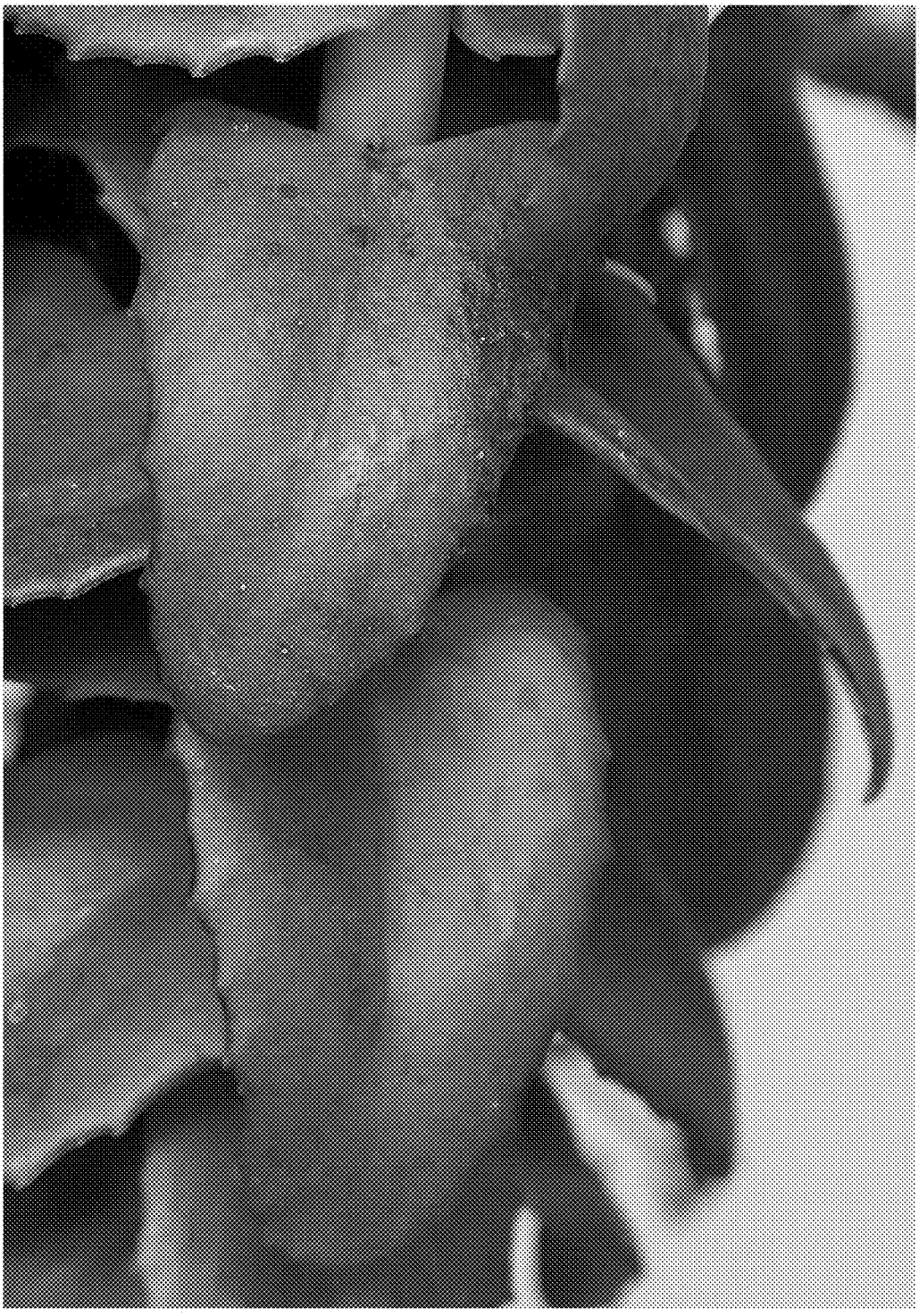

The photograph in FIG. 3 provides a close-up view of the foliage of 'PPC093'. The colors in the photographs may differ slightly from the color values cited in the detailed botanical description, which accurately describe the colors of the new *Sedum*.

DETAILED BOTANICAL DESCRIPTION

The following is a detailed description of the new cultivar as observed on 2-year-old plants of 'PPC093' as field grown in Zuidwolde, The Netherlands and placed in 27-cm containers for the descriptions. The phenotype of the new cultivar may vary with variations in environmental, climatic, and cultural conditions, as it has not been tested under all possible environmental conditions. The color determination is in accordance with the 6th edition, 2019 reprint of the 2015 Colour Chart of the Royal Horticultural Society, London, England, except where general color terms of ordinary dictionary significance are used.

General Description:

*Blooming period*.—Spring to autumn in The Netherlands.

*Plant type*.—Herbaceous perennial.

*Plant habit*.—Broadly upright, well-branched, short.

*Height and spread*.—Average of 60 cm in height and width as grown in the landscape.

*Hardiness*.—At least in U.S.D.A. Zones 5 to 9.

*Disease and pests*.—No susceptibility or resistance to diseases or pests has been observed.

*Root description*.—Fibrous, 155A.

*Propagation*.—Tissue culture (preferred) and stem cuttings.

*Growth rate*.—Moderately vigorous.

*Root development*.—Roots initiate in 6 weeks, a young plant can be produced in 2 months.

Stem Description:

*Stem shape*.—Rounded.

*Stem size*.—An average of 43.4 cm in length and 1.1 cm in width.

*Internode length*.—Average of 9 mm.

*Stem color*.—Young; 145B, upper surface suffused with 185A, mature; 144C, upper surface suffused with 187B.

*Stem surface*.—Matte, very thin waxy layer N187C in color.

*Stem habit*.—Average angle of 15°, very strong, average of 21 main branches, an average of 3 lateral branches per main branch.

Foliage Description:

*Leaf shape*.—Ovate.

*Leaf division*.—Simple.

*Leaf arrangement*.—Opposite and alternate, occasionally in whorls of three.

*Leaf base*.—Truncate.

*Leaf apex*.—Broad bluntly acute.

*Leaf venation*.—Pinnate, color upper surface N187B, color lower surface 145A.

*Leaf margins*.—Coarsely shallow dentate.

*Leaf attachment*.—Sessile.

*Leaf orientation*.—Outward.

*Leaf texture*.—Thick, succulent.

*Leaf surface*.—Both surfaces are smooth, glabrous, matte.

*Leaf color*.—Young upper and lower surface; 145A to 145C, edges towards the top; 183A, mature upper surface; a blend of N187A and 200A, covered with a very thin waxy layer N187B, mature lower surface; 137C and 137D, covered with a very thin waxy layer 191B.

*Leaf size*.—Average of 6.4 cm in length, 4 cm in width.

Flower Description:

*Inflorescence type*.—Compound cyme.

*Inflorescence size*.—An average of 10.4 cm in diameter, 13.3 cm height.

*Lastingness of inflorescence*.—At least one month.

*Flower type*.—Perfect, spreading, 5-starred.

*Flower number*.—An average of 225 flowers per inflorescence, 4,500 per plant.

*Flower fragrance*.—None.

*Flower buds*.—Ovate to nearly elliptic in shape, 5 mm length and 3 mm in width, glabrous and smooth surface, color; 145D, upper half strongly tinged 184C and 184D.

*Flower size*.—5 mm in depth, 3 mm in diameter.

*Peduncles*.—Round in shape, strong, an average of 7.6 cm in length and 3 mm in diameter, surface is moderately glossy, color; a blend of 145D and 150C, sunny side moderately to very strongly tinged 187C, covered with a very thin waxy layer 186C in color, average angle of main peduncle 0°, average angle of secondary peduncles 35°.

*Pedicels*.—Round in shape, moderately strong, an average of 2.5 mm in length and 1 mm in diameter, surface is glossy, glabrous, smooth, color; 147C, moderately to very strongly tinged 183B, covered with a very thin waxy layer 191C in color, terminal flower average of 0° to peduncle, pedicels of other flowers in an average angle of 20° to peduncle.

*Calyx*.—Rotate, 1.5 mm in length, 3 mm in width.

*Sepals*.—5, whorled, average of 1.5 mm in length, 1 mm in width, ovate in shape, entire margin, acute apex, broadly cuneate base, both surfaces matte, glabrous and smooth, color; when opening upper surface 145D, narrowly edged N186D, tip N186C, when opening lower surface 145C and 150D, narrowly edged and sparsely dotted 187B, tip 187A, when fully open upper surface 145D, narrowly edged N186D, tip N186C, when fully open lower surface a blend of 145C and 150D, narrowly edged and sparsely dotted 187B, tip 187A.

*Petals*.—5, whorled, 5.5 mm in length and 1.5 mm in width, narrowly ovate in shape, cuneate base, acute apex, surfaces are matte, glabrous, and smooth, entire margin, color: when opening upper side; a blend of 4D and 150D and lighter, upper half strongly tinged 185C and 185D, when opening lower surface; a blend of 4D and 150D and lighter, upper half moderately tinged 185D, tip is darker 185A, fully open upper surface; a blend of 4D and 150D and lighter, upper half moderately tinged 185C and 185D, fully open lower surface; a blend of 4D and 150D and lighter, upper half moderately tinged 185D, tipped darker; 185A, main vein 185A, base a blend of 4D and 150D.

Reproductive Organs:

*Pistils*.—5, 1 mm in length, stigma; 0.2 mm diameter, pointed, N170D in color, style; 0.75 mm in length, N170D in color, ovary; 1C in color.

*Stamens*.—5, filaments; 4.5 mm, NN155D in color, anther; ovate in shape, 1 mm in length, 0.6 mm in width, 171A in color, tipped 179A, pollen; very low in quantity, NN155A in color.

*Fruit*.—Fruit and seed production has not been observed to date.

It is claimed:

1. A new and distinct variety of *Sedum* plant named 'PPC093' as described and illustrated herein.

* * * * *